United States Patent
Grady et al.

(10) Patent No.: US 8,917,925 B1
(45) Date of Patent: *Dec. 23, 2014

(54) SYSTEMS AND METHODS FOR DATA AND MODEL-DRIVEN IMAGE RECONSTRUCTION AND ENHANCEMENT

(71) Applicant: HeartFlow, Inc., Redwood City, CA (US)

(72) Inventors: Leo Grady, Millbrae, CA (US); Michiel Schaap, Mountain View, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/291,465

(22) Filed: May 30, 2014

Related U.S. Application Data

(60) Provisional application No. 61/972,056, filed on Mar. 28, 2014.

(51) Int. Cl.
| | | |
|---|---|---|
| *G06K 9/00* | (2006.01) | |
| *G06T 5/00* | (2006.01) | |
| *G06T 5/50* | (2006.01) | |
| *A61B 8/14* | (2006.01) | |

(52) U.S. Cl.
CPC .. *G06T 5/001* (2013.01); *G06T 5/50* (2013.01)

USPC .......................................... 382/131; 600/458

(58) Field of Classification Search
CPC ................................... G06T 5/50; G06K 9/00
USPC ......... 382/128, 129, 130, 131, 132, 133, 134, 382/254, 266, 284; 600/36, 381, 458, 480, 600/482, 485, 500, 505; 623/1.14, 1.21, 623/903; 128/920, 922
See application file for complete search history.

(56) References Cited

U.S. PATENT DOCUMENTS

| | | | | |
|---|---|---|---|---|
| 7,933,436 | B2 * | 4/2011 | Gundel et al. | ................ 382/128 |
| 8,837,860 | B1 * | 9/2014 | Grady et al. | .................. 382/284 |

* cited by examiner

*Primary Examiner* — Abolfazl Tabatabai
(74) *Attorney, Agent, or Firm* — Bookoff McAndrews, PLLC

(57) ABSTRACT

Systems and methods are disclosed for image reconstruction and enhancement, using a computer system. One method includes acquiring a plurality of images associated with a target anatomy; determining, using a processor, one or more associations between subdivisions of localized anatomy of the target anatomy identified from the plurality of images, and local image regions identified from the plurality of images; performing an initial image reconstruction based on image acquisition information of the target anatomy; and updating the initial image reconstruction or generating a new image reconstruction based on the image acquisition information and the one or more determined associations.

20 Claims, 8 Drawing Sheets

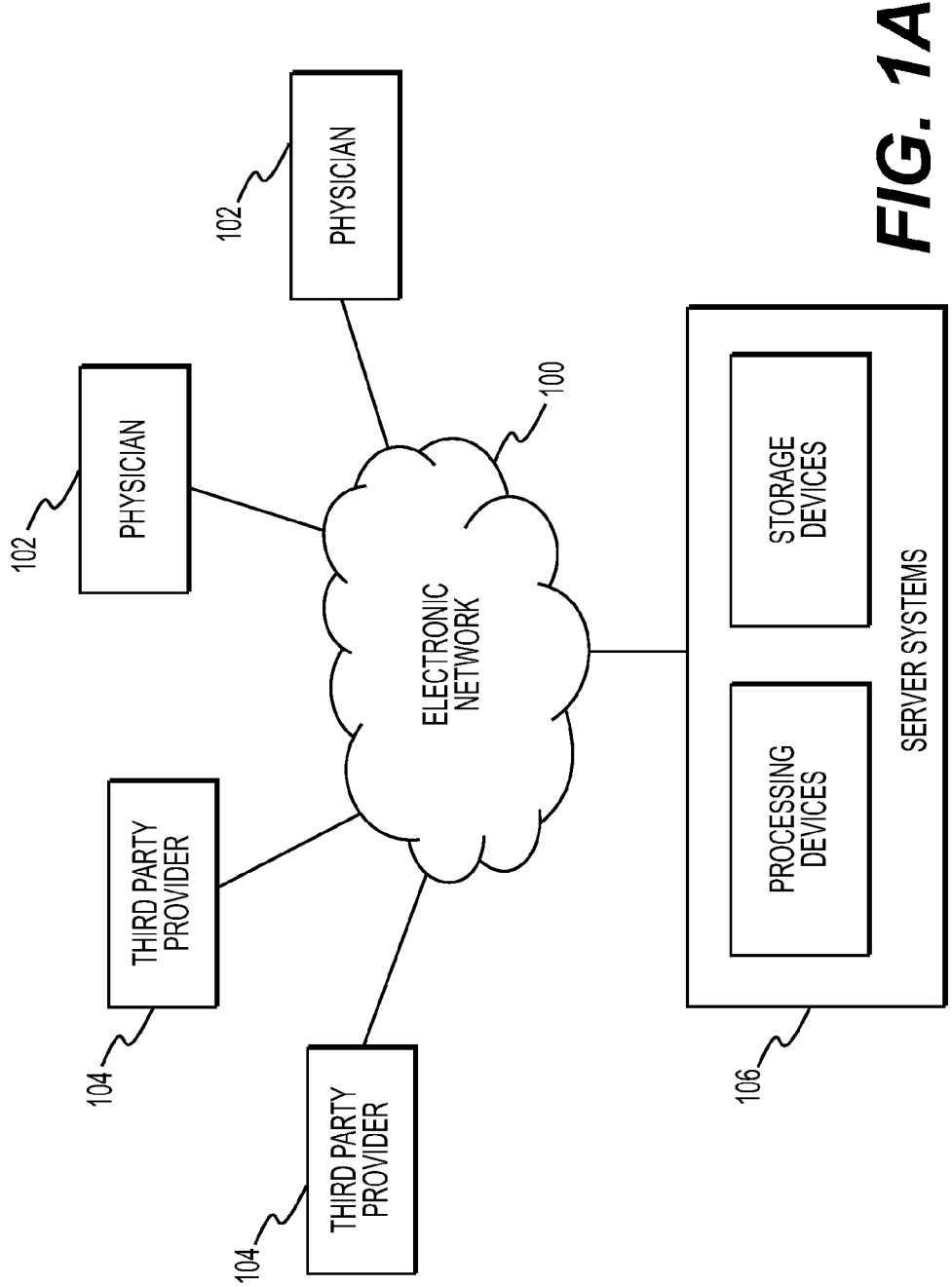

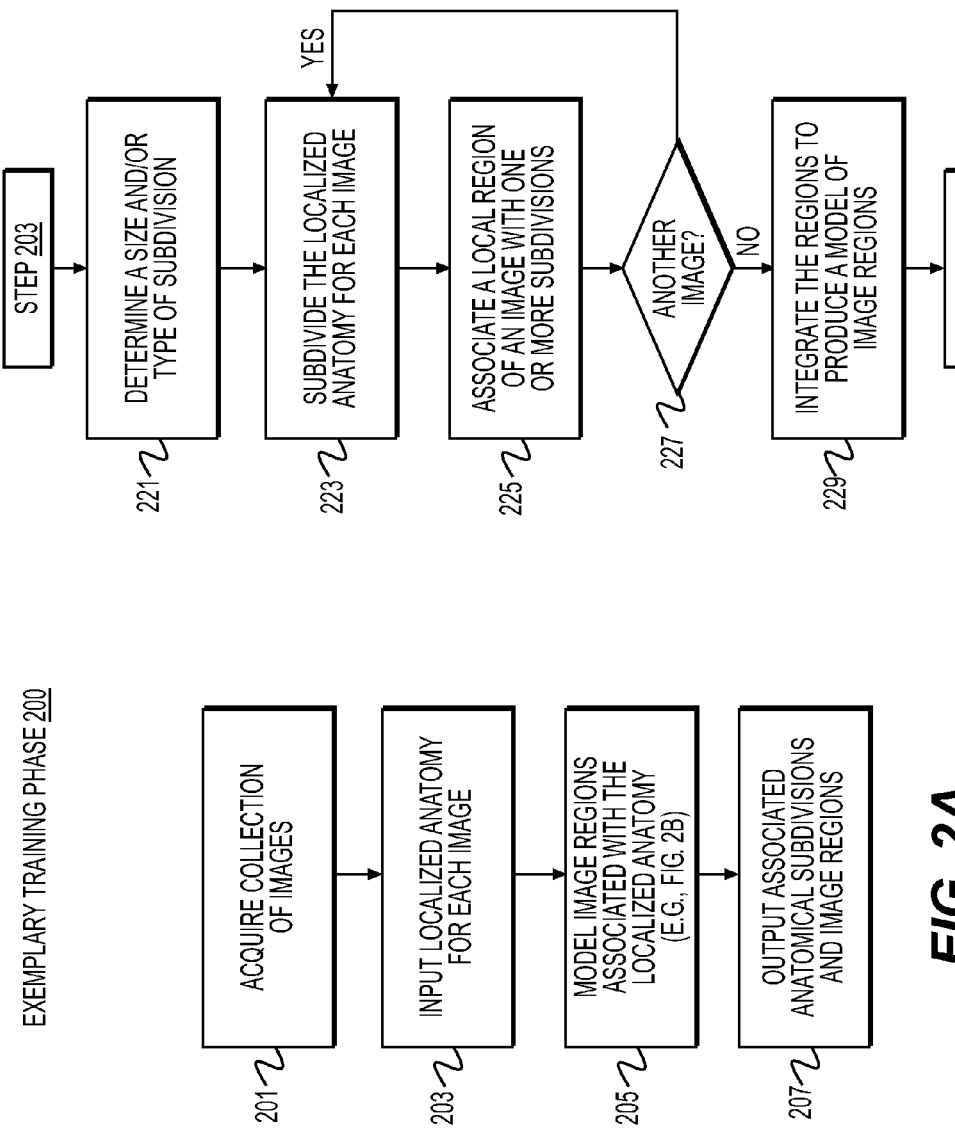

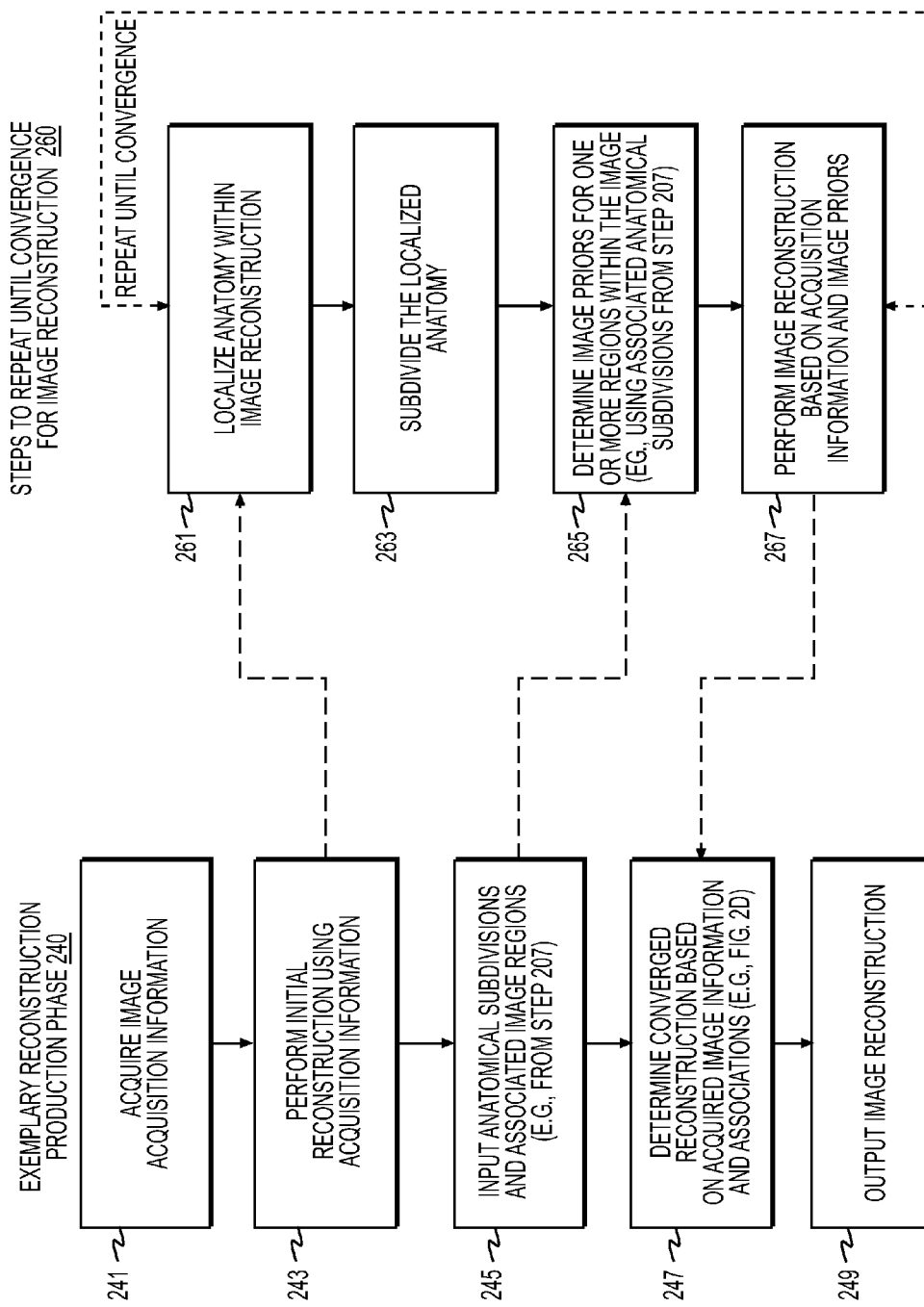

SYSTEMS AND METHODS FOR DATA AND MODEL-DRIVEN IMAGE RECONSTRUCTION AND ENHANCEMENT

RELATED APPLICATION(S)

This application claims priority to U.S. Provisional Application No. 61/972,056 filed Mar. 28, 2014, the entire disclosure of which is hereby incorporated by reference in its entirety.

FIELD OF THE INVENTION

Various embodiments of the present disclosure relate generally to medical imaging and related methods. More specifically, particular embodiments of the present disclosure relate to systems and methods for data and model-driven image reconstruction and/or enhancement.

BACKGROUND

Medical imaging and extraction of anatomy from imaging is important, as evidenced by the many means of medical imaging available. Several imaging techniques involve reconstruction and image enhancement on raw acquired data in order to produce better images. Reconstruction and enhancement may be used to decrease noise in an image, smooth the effects of incomplete data, and/or optimize imaging. Common forms of medical imaging that employ image reconstruction and/or enhancement include computed tomography (CT) scans, magnetic resonance imaging (MR), ultrasound, single positron emission computed tomography (SPECT), and positron emission tomography (PET). One mechanism used to achieve higher-quality reconstruction and enhancement is to use prior information about a target reconstructed/enhanced image. Typically, the prior information takes the form of assumptions about image smoothness or image patches from reference images.

Reference images are often available and used to obtain the prior information. Reference images may include at least a portion of a target anatomy, and portions of reference images may be used to render models of anatomy associated with the target anatomy. For example, reference images may be idealized images, images of a patient associated with a target anatomy (e.g., wherein a target anatomy may include an anatomical part of the patient), images of the anatomical part of other patients, etc. The images may be collected at various times or conditions, and they may have various levels of relevance or resemblance to a specific target anatomy.

Use of the reference images as image patches may mean that reference image use is piecemeal and/or may apply only to regions of an image identified as problematic. Evaluation of whether reference images are suitable for use as image patches may be lacking. In addition, use of reference images only as image patches may mean that unless portions of an image are identified as problematic, the image or various portions of the image may not have the opportunity to benefit from comparison to a reference image.

Accordingly, a need exists for systems and methods for reconstructing and enhancing images based on reference images and associated anatomical models.

SUMMARY

According to certain aspects of the present disclosure, systems and methods are disclosed for image reconstruction and enhancement. One method of medical image reconstruction includes: acquiring a plurality of images associated with a target anatomy; determining, using a processor, one or more associations between subdivisions of localized anatomy of the target anatomy identified from the plurality of images, and local image regions identified from the plurality of images; performing an initial image reconstruction based on image acquisition information of the target anatomy; and updating the initial image reconstruction or generating a new image reconstruction based on the image acquisition information and the one or more determined associations.

In accordance with another embodiment, a system for medical image reconstruction comprises: a data storage device storing instructions for image reconstruction and enhancement; and a processor configured for: acquiring a plurality of images associated with a target anatomy; determining, using a processor, one or more associations between subdivisions of localized anatomy of the target anatomy identified from the plurality of images, and local image regions identified from the plurality of images; performing an initial image reconstruction based on image acquisition information of the target anatomy; and updating the initial image reconstruction or generating a new image reconstruction based on the image acquisition information and the one or more determined associations.

In accordance with yet another embodiment, a non-transitory computer readable medium for use on a computer system containing computer-executable programming instructions for medical image reconstruction is provided. The method includes: acquiring a plurality of images associated with anatomy of a target anatomy; determining, using a processor, one or more associations between subdivisions of localized anatomy of the target anatomy identified from the plurality of images, and local image regions identified from the plurality of images; performing an initial image reconstruction based on image acquisition information of the target anatomy; and updating the initial image reconstruction or generating a new image reconstruction based on the image acquisition information and the one or more determined associations.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 1A is a block diagram of an exemplary system and network for image reconstruction and/or enhancement, according to an exemplary embodiment of the present disclosure.

FIG. 2A is a block diagram of an exemplary method for a training phase of image reconstruction and/or enhancement, according to an exemplary embodiment of the present disclosure.

FIG. 2B is a block diagram of an exemplary method for building a model of image regions associated with a localized anatomy, for use in a training phase of reconstruction and/or enhancement of medical images, according to an exemplary embodiment of the present disclosure.

FIG. 2C is a block diagram of an exemplary method of a production phase of reconstruction of medical images, according to an exemplary embodiment of the present disclosure.

FIG. 2D is a block diagram of an exemplary method for producing a converged image reconstruction, for use in a production phase of reconstructing medical images, according to an exemplary embodiment of the present disclosure.

DESCRIPTION OF THE EMBODIMENTS

Figure 1B:
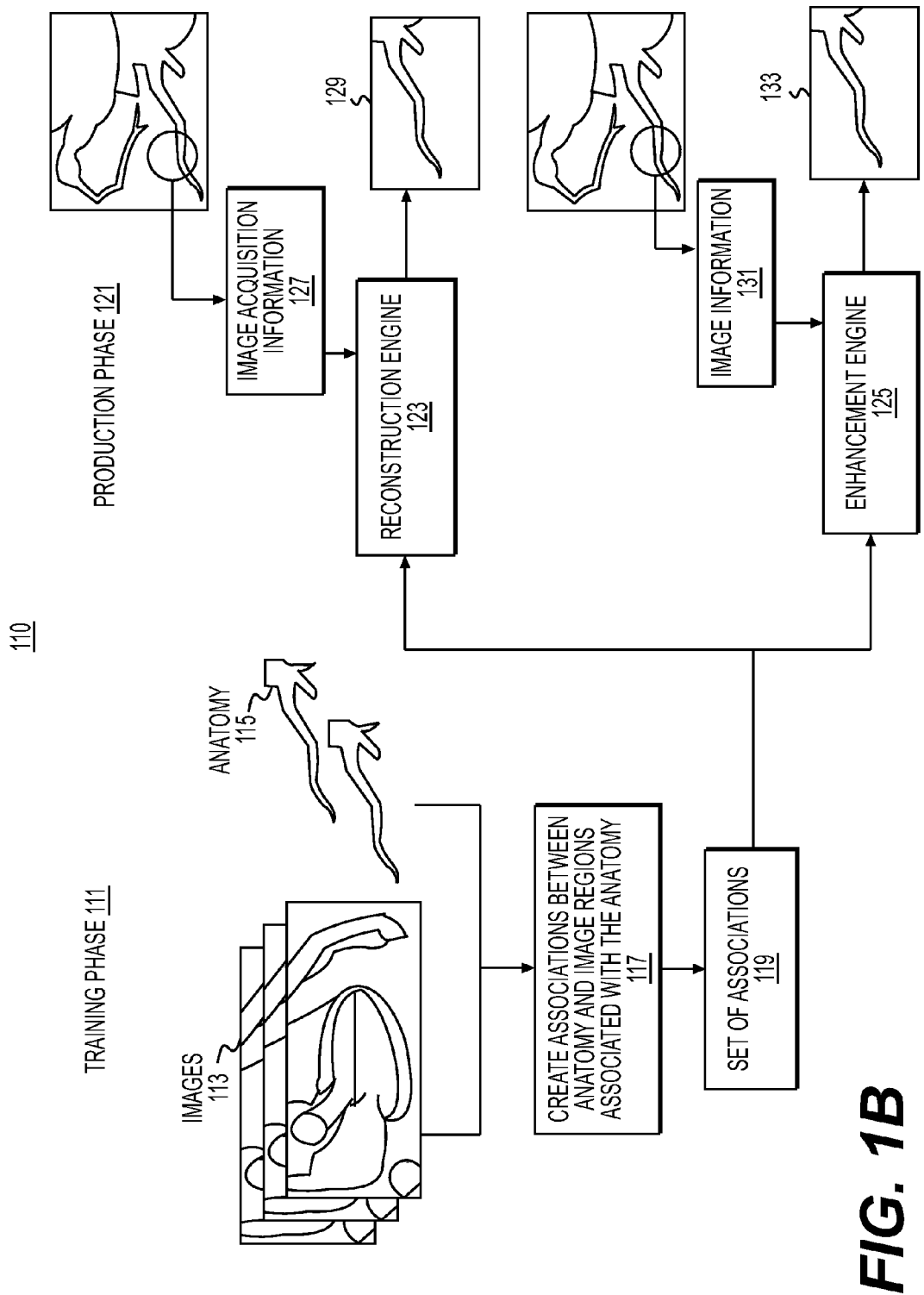
FIG. 1B is a block diagram of an exemplary overview of a training phase and production phase for image reconstruction and/or enhancement, according to an exemplary embodiment of the present disclosure.

Reference will now be made in detail to the exemplary embodiments of the invention, examples of which are illustrated in the accompanying drawings. Wherever possible, the same reference numbers will be used throughout the drawings to refer to the same or like parts.

As described above, the use of reference images as image patches for medical image reconstruction and/or enhancement may involve using a portion of a reference image to compensate for deficits in a constructed image. However, the reference images may have little or no impact on other parts of the constructed image. Thus, the present disclosure is directed to systems and methods for data and model-driven image reconstruction and enhancement using target anatomy reference images as more than image patches. In other words, the present disclosure is directed to improving image reconstruction and/or enhancement by incorporating into image reconstruction and/or enhancement, associations between anatomical subdivisions and image regions available from reference images.

The present disclosure is directed to a new approach for reconstruction and/or enhancement of a target anatomy image using prior information about a target reconstructed/enhanced image, where the information includes associations between reference image regions and parts of the target anatomy, such as anatomical features extracted from or identified in the image regions. In one embodiment, the present disclosure may include both a training phase and a production (and/or usage phase) for use in a method of image reconstruction, as well as a method of enhancing images. In one embodiment, the training phase for both image reconstruction and image enhancement may include developing a set of known or knowable associations between anatomy and image renderings. For example, in general, the training phase may involve receiving a collection of images, receiving or inputting information of an anatomical part or portion shown in each of the images (e.g., a localized anatomy for each of the images), and building a model of image regions associated with respective portions of the localized anatomy. An output from the training phase may include a set of anatomical subdivisions associated with image regions.

In general, the production phase for reconstructions may include using the set of anatomical subdivisions associated with image regions (from the training phase) in conjunction with image acquisition information for a particular target anatomy, e.g., a particular patient or individual, in order to create a more accurate and/or better-informed image reconstruction. In one embodiment, image reconstruction may be based on acquired images and/or image acquisition information, and image enhancement may be based on any image information. The production phase for image enhancement may then include using the set of anatomical subdivisions associated with image regions along with image information to output an enhanced image.

Referring now to the figures, FIG. 1A depicts a block diagram of an exemplary environment of a system and network for data and model-driven image reconstruction and enhancement. Specifically, FIG. 1A depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of one or more patients' cardiac, vascular, and/or organ systems. The physicians 102 and/or third party providers 104 may also obtain any combination of patient-specific information, such as age, medical history, blood pressure, blood viscosity, etc. Physicians 102 and/or third party providers 104 may transmit the cardiac/vascular/organ images and/or patient-specific information to server systems 106 over the electronic network 100. Server systems 106 may include storage devices for storing images and data received from physicians 102 and/or third party providers 104. Server systems 106 may also include processing devices for processing images and data stored in the storage devices. Alternatively or in addition, the data and model-driven image reconstruction and enhancement of the present disclosure (or portions of the system and methods of the present disclosure) may be performed on a local processing device (e.g., a laptop), absent an external server or network.

FIG. 1B is a diagram of an overview 110 of an exemplary training phase and an exemplary production phase for image reconstruction and enhancement, according to an exemplary embodiment of the present disclosure. In one embodiment, the systems and methods for image reconstruction and/or enhancement may include a training phase 111 and a production phase 121. In general, the training phase 111 may involve generating associations between anatomical subdivisions and image regions. The production phase 121 may generally then use the associations to determine image priors for regions within a reconstruction or, in the case of an image enhancement, a previously provided image.

In one embodiment, the training phase 111 may begin with receiving inputs of images 113 and known anatomy 115. Images 113 may include images from any known medical imaging modality (e.g., CT, MR, SPECT, etc.). Anatomy 115 may be 2-D, 3-D, or other geometric models of human anatomy. In other words, images 113 may include representations of anatomy 115, and/or anatomy 115 may show or represent geometry of some portion of anatomy rendered in images 113. For example, anatomy 115 may include models of anatomy, expected anatomy, etc. that are shown (or expected to be shown) in the images 113. Models of common anatomy rendered between images 113 and anatomy 115 and/or a region of interest in both images 113 and anatomy 115 may be referred to as "localized anatomy" within each of the images 113. In one embodiment, the associated images 113 and anatomy 115 may be obtained from the same individual for whom images are to be reconstructed and/or enhanced in a production phase. In some cases, one individual or patient may be the source of multiple pairs or even all of the pairs of associated images 113 and anatomy 115. In some cases, each associated image 113 anatomy 115 pair may be obtained from a different individual or patient. Given the input of images 113 and anatomy 115, the training phase 111 may then include step 117 of creating associations between portions of anatomy 115 and regions of images 113. Specifically, as described in more detail below, step 117 may include identifying a region or subset of an image 113, identifying a region or subset of a paired anatomy 115, and associating the region or subset of the image 113 with the region or subset of the anatomy 115. The training phase 111 thus produces output 119, which includes a set of associations between portions of anatomy 115 and regions of images 113.

Output 119 may be used as an input to an exemplary production phase 121, where reconstruction engine 123 and enhancement engine 125 may determine image priors based on output 119 for use in producing reconstructed and/or enhanced images of a particular individual or patient. For example, reconstruction engine 123 may receive image acquisition information 127 of an area of anatomy for a particular patient. Using image acquisition information 127 along with image priors determined from output 119, reconstruction engine 123 may produce reconstruction 129. For image enhancements, enhancement engine 125 may receive image information 131. Enhancement engine 125 may then produce image enhancement 133 based on image information 131 and image enhancements determined from output 119.

Figure 2E:
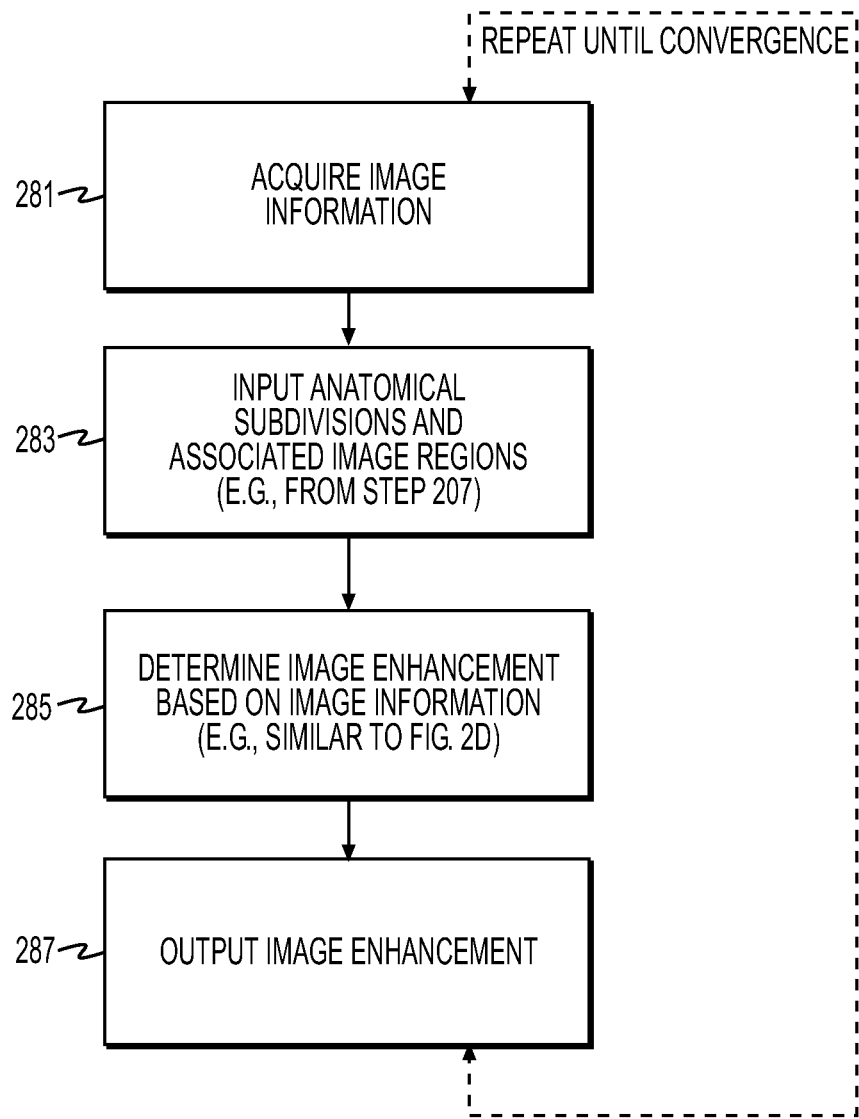
FIG. 2E is a block diagram of an exemplary method a production phase for producing an enhancement of medical images, according to an exemplary embodiment of the present disclosure.
Figures 3A, 3B:
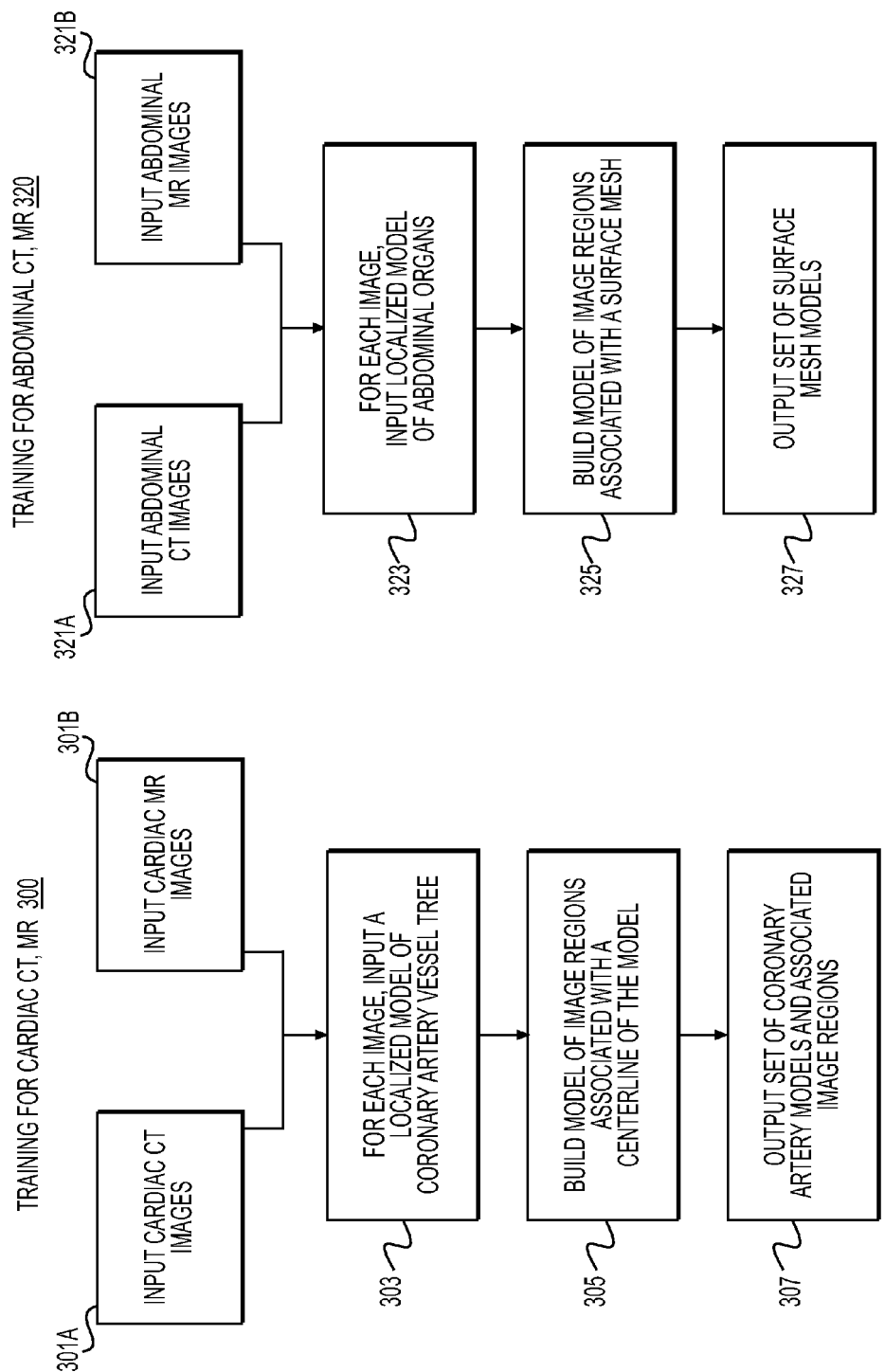
FIG. 3A and FIG. 3B are block diagrams of exemplary training methods for iterative reconstruction of images, according to an exemplary embodiment of the present disclosure.
Figure 4A:
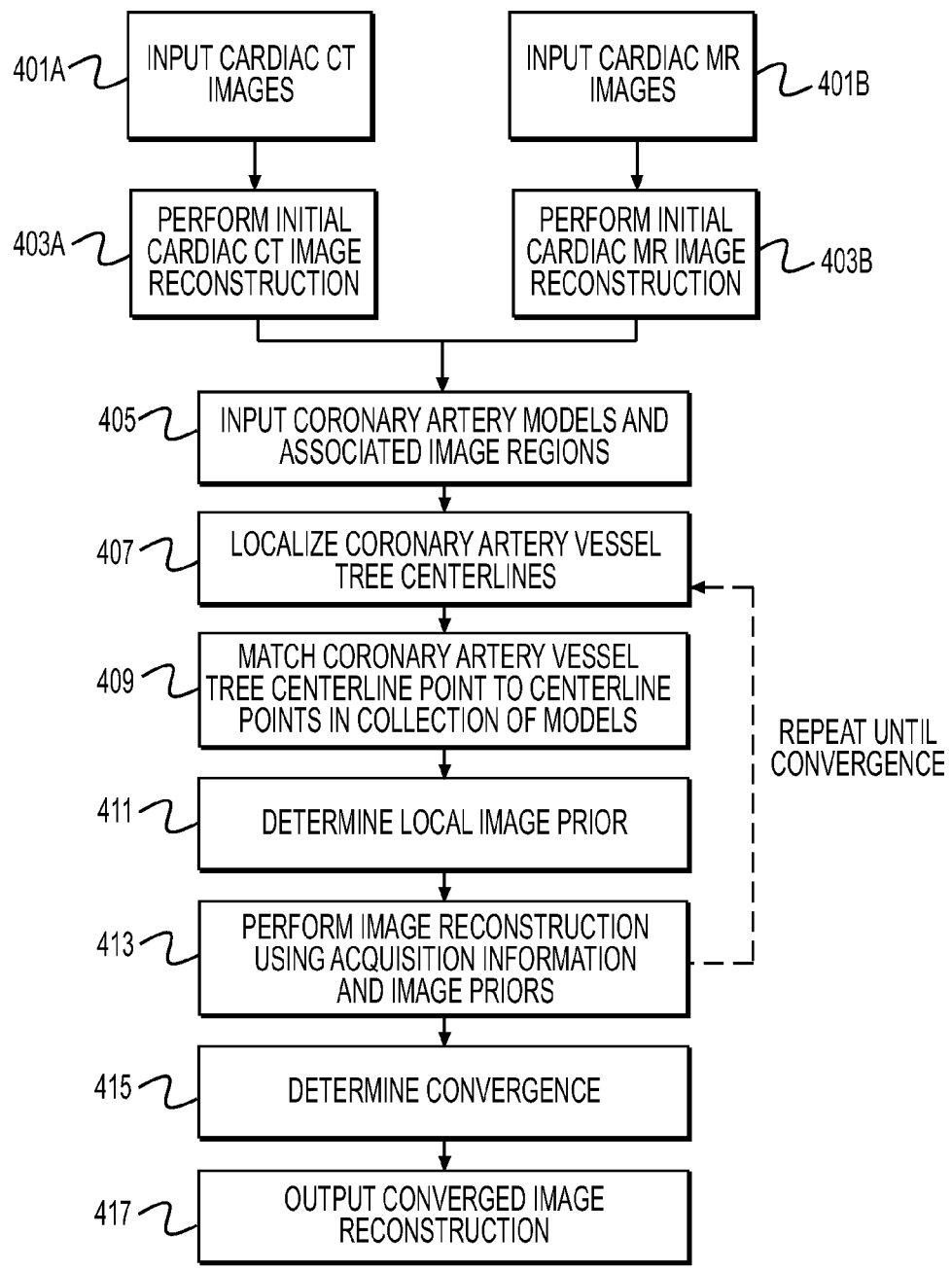
FIG. 4A and FIG. 4B are block diagrams of exemplary methods for producing reconstructions, according to an exemplary embodiment of the present disclosure.
Figure 4B:
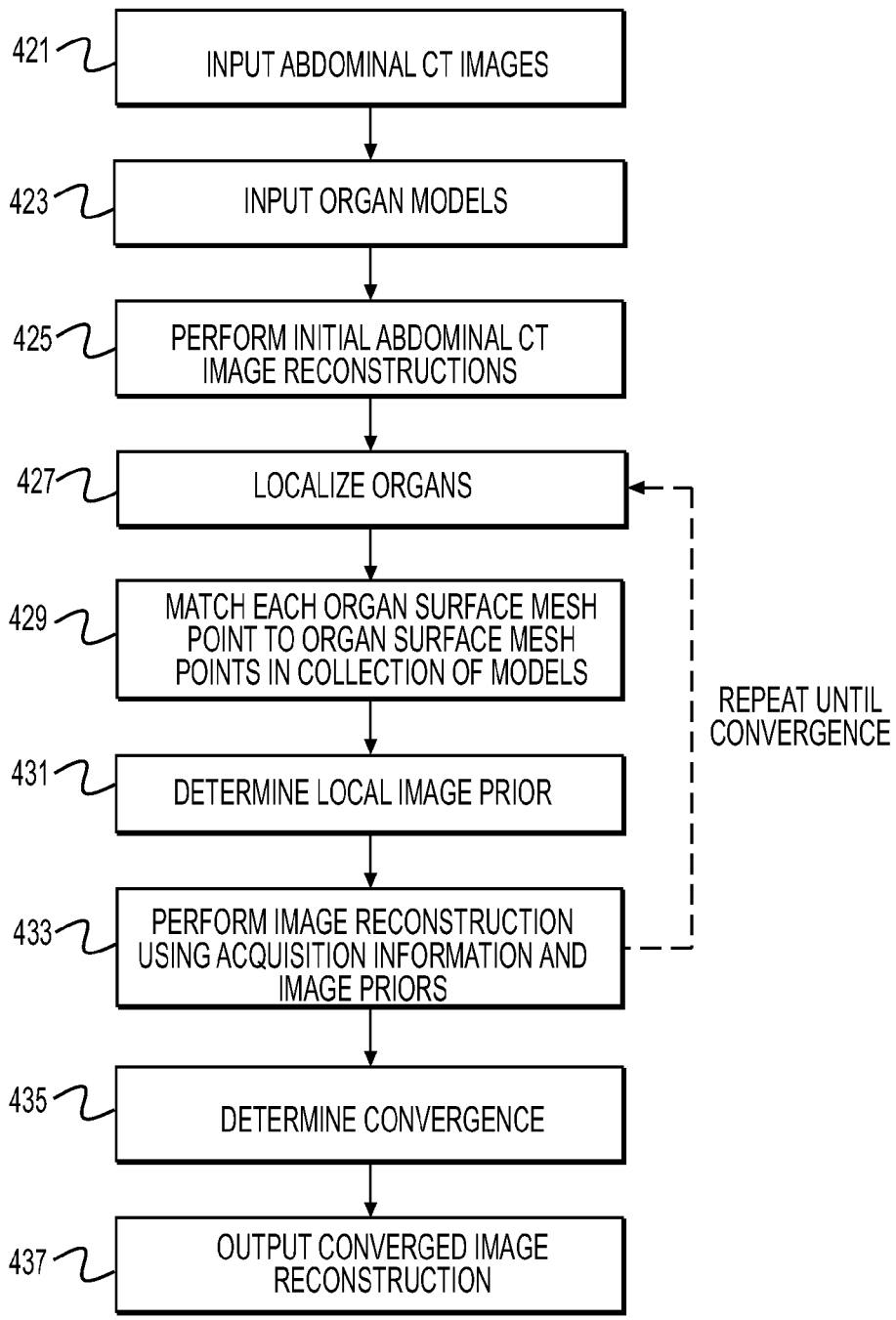

FIGS. 2A and 2B depict flowcharts of exemplary embodiments of the training phase 111 of FIG. 1B. FIGS. 2C-2E depict flowcharts of exemplary production phases for image reconstruction and image enhancement. FIGS. 3A and 3B depict flowcharts of exemplary embodiments of training phases as applied to cardiac and abdominal images, respectively. FIGS. 4A and 4B depict flowcharts of exemplary embodiments of production phases for cardiac and abdominal images, respectively, in which the training phase from FIG. 3A may provide an input for the production phase of FIG. 4A, and the training phase of FIG. 3B may be associated with the production phase of FIG. 4B.

FIG. 2A is a block diagram of an exemplary training phase for producing a model of image regions associated with anatomy portions for both reconstruction and enhancement of medical images, according to an exemplary embodiment. In one embodiment, while the procedures for production in image reconstruction and production in image enhancement may differ in some respects, the procedure for a training phase may, in some cases, be the same for both image reconstruction and image enhancement. A model of image regions relied upon for the reconstruction and enhancement may be generated the same way. In other words, models of image regions for image reconstruction and enhancement may both include, or be based on, a set of known or created associations between anatomical subdivisions and corresponding image regions. The set of associations may represent an understanding of an image region being a representation of a portion of an anatomy, and in some embodiments, an understanding of the identity of the person having that portion of the anatomy. The training phase may develop a model of relationships between images and anatomy, based on a collection of images. In this way, a model of image regions developed from the training phase may form a basis of expected image regions in relation to portions of anatomy, thus providing guidance for image reconstruction and enhancement. FIG. 2B depicts an embodiment of certain steps of the method of FIG. 2A, including exemplary detailed steps for building a model of associations between image regions and anatomy, according to one embodiment.

FIG. 2C depicts steps of an exemplary production phase for an image reconstruction, according to an exemplary embodiment. FIG. 2D depicts an embodiment of certain exemplary steps of the method of FIG. 2C, including certain steps that may be repeated until convergence in order to produce the image reconstruction output by the method of FIG. 2C. FIG. 2E includes a production phase for an image enhancement. The steps in FIG. 2C may be similar to those of the method of FIG. 2E, except that the steps for FIG. 2E may not necessarily be based on an acquired image. Rather, since FIG. 2E addresses image enhancement, an image may be already available and need not be acquired and/or created in an independent step.

As introduced above, FIG. 2A is a block diagram of an exemplary method 200 of a training phase for reconstruction or enhancement of medical images, according to an exemplary embodiment of the present disclosure. Method 200 may be performed by server systems 106, based on information, images, and data received from physicians 102 and/or third party providers 104 over electronic network 100. The method of FIG. 2A may include receiving a collection of images (step 201). The collection of images may include or be associated with a target anatomy, for example, an anatomical feature of one or more individuals. A target anatomy may be any image and/or portion of an image that may undergo analysis and/or be used for analysis. In one embodiment, the images may be stored, input, and/or received on an electronic storage device.

In one embodiment, method 200 may further include receiving or inputting, for each image of the collection, a localized anatomy model of anatomy reflected within the image (step 203). For example, the localized anatomy may include a portion of an anatomy to be reviewed or analyzed. For instance, a target anatomy may include a patient's heart, where a localized anatomy may include a localized model of a coronary artery vessel tree. In one embodiment, the localized anatomy within the image may be received on an electronic storage device.

Next, step 205 may include building a model of image regions associated with portions of the localized anatomy. In one embodiment, the model may be built using a computational device. Exemplary methods of building the model are further described in FIG. 2B. Given the model, a set of associated anatomical subdivisions and image regions may be produced. Such a set of associated anatomical subdivisions and image regions may be output to an electronic storage device (step 207).

FIG. 2B is a block diagram of an exemplary method 220 for building a model of image regions associated with respective/corresponding portions of localized anatomy in a training phase for reconstruction or enhancement of medical images, according to an exemplary embodiment of the present disclosure. In one embodiment, method 220 is one way of carrying out step 205 of modeling associations between image regions and portions (e.g., subdivisions) of localized anatomy. Method 220 may be performed by server systems 106, based on information, images, and data received from physicians 102 and/or third party providers 104 over electronic network 100. In other words, the model of image regions may be built using a computational device.

In one embodiment, step 221 may include determining a size and/or type of subdivision for a target anatomy in the images. For example, a subdivision may be a single component encompassing an entire localized anatomy. Alternately, subdivisions may be very small relative to the image. Step 221 may include determining a level of granularity in the size of the subdivisions. In some embodiments, the size of subdivisions may be static or dynamic. For example, step 221 may include adjusting sizes of subdivisions in view of image resolution, sensitivity, etc.

In one embodiment, method 220 may further include step 223 of subdividing the localized anatomy into one or more subdivisions, for each image and localized anatomy in the collection (e.g., the collection of images received at step 201). For example, the subdivisions may be uniform across the entire image and localized anatomy, throughout the collection. In another example, the subdivisions may vary, depending on a local region of the anatomy.

In one embodiment, step 225 may include associating a local region of an image with the one or more subdivisions of the anatomy. In other words, regions of the images may not be directly identified as being associated with a localized anatomy or one or more subdivisions of the localized anatomy. Step 225 may create associations between the regions of images and the one or more subdivisions, such that the local regions of the images may be recognized as being associated with subdivisions that correspond to the same localized anatomy. In one embodiment, step 227 may include an option to determine whether another image is available in the collection of images (e.g., from step 201). If more images remain in the collection, the method may continue to subdivide the localized anatomy in the image (step 223) and associate a local region of an image with one or more subdivisions (step 225). If all of the images in the collection have been through steps 223 and 225, results of the subdividing and image association may be processed in step 229. In one embodiment, step 229 may include combining or integrating a set of the local regions of the image that are associated with the one or more subdivisions. In integrating the set, step 229 may build a model of image regions associated with respective portions of an anatomy.

FIG. 2C is a block diagram of an exemplary method 240 for producing a reconstruction of medical images, according to an exemplary embodiment of the present disclosure. Method 240 may be performed by server systems 106, based on information, images, and data received from physicians 102 and/or third party providers 104 over electronic network 100. In one embodiment, method 240 may be based on output from the training phase, for example, method 200 (including method 220).

In one embodiment, method 240 may include step 241 of receiving image acquisition information, for instance, on an electronic storage device. In one embodiment, step 243 may include performing an initial image reconstruction based on the acquisition information from step 241. The reconstruction may be performed using any reconstruction method known in the art. Step 245 may include receiving a set of associated anatomical subdivisions and associated image regions (e.g., from step 207 of the method 200 of a training phase). The set of associated anatomical subdivisions and associated image regions may be received on an electronic storage device.

Next for step 247, a converged reconstruction may be created using the initial reconstruction, in conjunction with the set of anatomical subdivisions and associated image regions (e.g., from step 245). Exemplary steps for creating the converged reconstruction may be found at FIG. 2D. Then, method 240 may further include outputting the converged image reconstruction, for example, to an electronic storage device and/or display (step 249).

FIG. 2D is a block diagram of an exemplary method 260 for producing the converged image reconstruction (e.g., of step 247), according to an exemplary embodiment of the present disclosure. In other words, the steps of method 260 may be repeated until images converge, thus forming an image reconstruction (e.g., the converged reconstruction). Method 260 may be performed by server systems 106, based on information, images, and data received from physicians 102 and/or third party providers 104 over electronic network 100.

In general, method 260 of FIG. 2D may include localizing anatomy within an initial image reconstruction, subdividing the localized anatomy, and performing image reconstruction using the image acquisition information and image priors, where the reconstruction is based on expected associations between subdivisions and image regions developed from the training phase. In one embodiment, step 261 may include localizing anatomy within an image reconstruction, e.g., the initial image reconstruction from step 243. For example, out of an image reconstruction, step 261 may include determining an anatomy that is part of the image and pinpointing the anatomy for analysis. Then, step 263 may include subdividing the localized anatomy into one or more subdivisions. In one embodiment, the subdivisions may be uniform, while in another embodiment, subdivisions may vary across the localized anatomy. In yet another embodiment, subdivisions of the localized anatomy for step 263 may differ from subdivisions defined in the training phase (e.g., step 223). Step 265 may include determining image priors for one or more regions within the image reconstruction, wherein the image priors may be based on the set of associated anatomical subdivisions and image regions from the training phase (e.g., from step 207). In one embodiment, the set from step 207 may be the input from step 245. In one embodiment, step 267 may then include performing an image reconstruction using acquisition information (e.g., from step 241) and image priors (e.g., from step 265).

From this image reconstruction from step 267, steps 261-267 may then repeat until convergence. For example, method 260 may repeat such that the reconstruction of step 267 is used as input, wherein anatomy within the reconstruction from step 267 is localized (e.g., step 261), this anatomy is subdivided (e.g., step 263), image priors are found (and/or updated) from regions within the reconstruction (e.g., step 265), and a new (and/or updated) image reconstruction is produced from the acquisition information and found/updated image priors. In short, method 260 may provide one way of producing an image reconstruction from the inputs outlined in method 240. Upon convergence, step 247 may register the convergence and determine and/or receive the converged reconstruction.

As previously stated, method 240 (and method 260) for producing a reconstruction may be analogous to a method for enhancing images. While the methods may be similar, deviations between the production phase for image enhancement versus the production phase of reconstructions are explained in more detail below.

FIG. 2E is a block diagram of an exemplary method 280 for producing an enhancement of medical images, according to an exemplary embodiment of the present disclosure. Method 280 may be performed by server systems 106, based on information, images, and data received from physicians 102 and/or third party providers 104 over electronic network 100. In one embodiment, method 280 of producing an enhancement may differ from method 240 of producing a reconstruction in that an enhancement is an improvement of an available image.

Therefore, in one embodiment, method 280 does not include steps of acquiring images or creating an initial image. Rather, step 281 may start at receiving image information, as opposed to step 241 of receiving image acquisition information. In one embodiment, step 281 may include receiving image information, for example, on an electronic storage device. Step 283 may be similar to step 245 in that a set of associated anatomical subdivisions and associated image regions may be received, based on a training phase. Again, this set of associated anatomical subdivisions and associated image regions may be received from an electronic storage device.

Since method 280 includes an enhancement, an image is already available and a step of generating an initial image (e.g., step 243) may be unnecessary. In one embodiment, step 285 of performing image enhancement may include localizing anatomy within the image being enhanced, subdividing the localized anatomy into one or more subdivisions, using the set of associated anatomical subdivisions and image regions (e.g., from step 283) as image priors for one or more regions within the image, and performing image enhancement using image information (e.g., from step 281) and the image priors (e.g., from step 283). Then, step 287 may include outputting an enhanced image, for example, to an electronic storage device and/or display.

FIGS. 3A, 3B, 4A, and 4B are directed to specific embodiments or applications of the exemplary methods discussed in FIGS. 2A-2E. For example, FIG. 3A and FIG. 3B depict exemplary training phase methods for iterative reconstruction of cardiac and abdominal images, respectively, according to various embodiments. FIG. 3A may further provide the basis for a training phase method for cardiac image enhancement. FIGS. 4A and 4B, respectively, include exemplary production phase methods for iterative reconstruction of cardiac and abdominal images. FIG. 4A may additionally provide a basis for a production phase method for cardiac image enhancement. In some embodiments, the output of coronary artery models and associated image regions from the training phase of FIG. 3A may serve as an input for a cardiac image reconstruction production phase as shown in FIG. 4A. Similarly, surface mesh models and associated image regions output from FIG. 3B may be used toward a creating a converged image reconstruction from the production phase of FIG. 4B. While the embodiments for cardiac and abdominal images are presented as separate embodiments, the methods applied may be combined into reconstructions and/or enhancements that simultaneously include various anatomical parts.

FIG. 3A is a block diagram of an exemplary method 300 for iterative reconstruction of, specifically, cardiac images, according to various embodiments. For the method 300, cardiac images may include CT images and/or MR images. In one embodiment, step 301A may include inputting or receiving a collection of cardiac CT images, for example, on an electronic storage device. Iterative reconstruction for producing a cardiac CT image may allow for producing a cardiac CT image with a lower radiation dose by acquiring fewer samples and using prior information to reconstruct a complete CT image. Another embodiment may include step 301B of inputting or receiving a collection of cardiac MR images, for example, on an electronic storage device. For production of cardiac MR images, partial or parallel reconstruction allows for faster acquisition time by acquiring fewer samples and using prior information to reconstruct a complete MR image.

In one embodiment, step 303 may include inputting or receiving, for each image, a localized model of a coronary artery vessel tree within that image, for example, on the electronic storage device. The coronary artery vessel tree model may include centerlines of vessels that are sampled at discrete points. Step 305 may include building a model of image regions associated with one or more points along one or more centerlines. For example, for each image in the collection, a geometric (e.g., square or rectangular) region of the image may be associated with each centerline point in a model. In one case, the geometric region may be a 5 mm 3-D geometric region. The size of the image region for associating with a centerline point in a model may be static and/or dynamic, depending, at least, on the images, density of centerline points, processing power, etc. In one embodiment, step 305 of building a model may be performed by a computational device. Final step 307 may include outputting a set of coronary artery models and associated image regions, for example, to an electronic storage device.

In one embodiment, the training phase for image enhancement of a cardiac CT image may be similar to the training phase for iterative reconstruction of cardiac CT images. Image enhancement may be a method for using prior information to produce cardiac CT images with improved image quality and interpretability. One possible distinction may be inputting a collection of good quality cardiac CT images (e.g., on an electronic storage device), rather than inputting any collection of cardiac CT images. The training phase for image enhancement may focus on improving an image using the foundation of good quality cardiac images, whereas iterative reconstruction may provide a set of coronary artery models and associated image regions for a specific patient. Remaining steps for image enhancement of a cardiac CT image may include similarities to those for iterative reconstruction, in one exemplary embodiment. For example, image enhancement may also include inputting, for each image (of the collection of good quality cardiac CT images), a localized model of a coronary artery vessel tree within that image on an electronic storage device. The coronary artery vessel tree model may include centerlines of vessels sampled at discrete points. A computational device may then be used to build a model of image regions associated with the centerlines by, for example, associating a 5 mm 3-D geometric (e.g., rectangular) region of an image with each centerline point in a model. Afterwards, a set of coronary artery models and associated image regions may be output to an electronic storage device.

FIG. 3B is a block diagram of an exemplary method 320 for iterative reconstruction of abdominal CT images, according to one embodiment. Iterative reconstruction may permit production of an abdominal CT image with a lower radiation dose, for example, by acquiring fewer samples and using prior information to reconstruct a complete CT image. In one embodiment, step 321A may include inputting or receiving a collection of abdominal CT images, for example, on an electronic storage device. Alternately or in addition, step 321B may include inputting or receiving abdominal MR images, perhaps also on an electronic storage device. For each image, step 323 may include inputting a localized model of abdominal organs (e.g., liver, kidney, spleen, gall bladder, etc.) within that image (e.g., on the electronic storage device). The organ models may include surface meshes that are sampled at discrete points. In one embodiment, step 325 may include building a model of image regions associated with the surface mesh points. For example, for each image in the collection, step 325 may include associating a geometric region of the image with each surface mesh point in the model. In one case, the geometric region may be a 5 mm 3-D rectangular region of the model. In one embodiment, a computational device may be used to perform step 325. Step 327 may include outputting a set of surface mesh models and associated regions, for example, to an electronic storage device.

FIG. 4A and FIG. 4B include exemplary methods for producing reconstructions, according to an exemplary embodiment. With slight modifications, the method shown in FIG. 4A may serve as an exemplary method for producing image enhancement. FIG. 4A is a block diagram of an exemplary method 400 for producing iterative reconstruction of cardiac images, according to one embodiment. For example, step 401A may include inputting cardiac CT image acquisition information, for example, on an electronic storage device. Alternately, an input may include inputting cardiac MR image acquisition information, for example, on an electronic storage device (step 401B). For instance, acquisition information may include a set of lines in k-space acquired by one or more coils. Then, step 403A may include performing an initial cardiac CT image reconstruction using the acquisition information (e.g., input from step 401A) and any known iterative CT reconstruction technique. Analogous step 403B may pertain to an input of cardiac MR image acquisition information (rather than cardiac CT image acquisition information), where step 403B may include performing an initial cardiac MR image reconstruction using the acquisition information (e.g., from step 401B) and any known parallel/partial MR reconstruction technique. In one embodiment, step 405 may include inputting a set of coronary artery models and associated image regions from the training phase (e.g., on an electronic storage device).

Following step 405, step 407 may include localizing the coronary artery vessel tree centerlines within the image reconstruction, for instance, using any technique known to one of ordinary skill in the art. Step 409 may then include matching each coronary artery vessel tree centerline point found in the image to zero or more coronary artery vessel tree centerline points in the collection of coronary artery models input from step 403. The matching may be performed using any graph matching technique to compute metric(s) that may describe similarity between the coronary artery vessel tree centerline point and each point in the collection. Exemplary metrics include spectral correspondence, minimum edit distance, etc. In one case, spectral correspondence may include a spectral method for finding consistent, geometric matches or correspondence between two sets of features (e.g., meshes, shapes, numbers, points, vertices, etc.). Minimum edit distance may include the lowest count of operations that would change one point to another, specifically, the coronary artery vessel tree centerline point to each point in the collection. In one case, step 407 may further include determining a threshold value for the metric(s) that describe the similarity. In doing so, a collection of matched points may be created, where the matched points may contain zero or more matched points.

In one embodiment, step 411 may include determining a local image prior for each centerline point. In other words, each centerline point may have an image prior that is local to that particular point. Local image priors may be image priors that include particular anatomical objects of interest. In one embodiment, the local image prior may be determined by merging image regions associated with the zero or more matched points in the collection of matched points. If no matched points exist for a centerline point, the point may have no associated local image prior.

In one embodiment, merging may be achieved via several methods. In one instance, merging may entail averaging associated image regions. Another method of merging may include performing weighted averaging of associated image regions. For example, weights may be determined by the similarity metric of the associated points or the predetermined image quality of the image, from which the associated image region was originally drawn. An additional method of merging may include choosing an associated image region with greatest similarity to an image region local to the centerline point in the current image reconstruction. Yet another method of merging may include a sparse linear combination of the associated image regions that best match the image region local to the centerline point in the current image reconstruction.

Next, step 413 may include performing an image reconstruction using the acquisition information and image priors. For example, step 413 may include blending image priors within a current reconstruction. In one case, such blending may include applying an alpha compositing between the priors and the reconstructed image. In another instance, step 413 may include, for optimization-based iteration reconstruction methods, adding an extra term into the optimization that may penalize differences between the reconstructed image and local priors. Step 415 may include determining convergence of the iterative process of steps 407-413. For example, step 415 may include measuring the difference between a reconstructed image during two successive iterations (e.g., by computing a mean squared difference between the intensity values at all voxels) and converging if the difference is below a predetermined threshold. Then, step 417 may include outputting a converged image reconstruction, for example, to an electronic storage device and/or display. In one embodiment, steps 403A and/or 403B through step 415 may be performed using a computational device.

Image enhancement of a cardiac CT image may be similar in certain respects to method 400, except that in some cases the initial step includes inputting a cardiac CT image, rather than cardiac CT image acquisition information. In one instance, the cardiac CT image may be input on an electronic storage device. As previously discussed, the distinction between the input for enhancement versus reconstruction may be because an image is already available to be enhanced. In addition, step 403A may be unnecessary for image enhancement, since an image and/or reconstruction may already be available. Again, image enhancement may not necessarily include performing an initial image reconstruction because image enhancement inherently already includes an available image. In other words, production of image enhancement may include inputting or receiving a cardiac CT image on an electronic storage device and then inputting a set of coronary artery models and associated image regions from the training phase (e.g., on an electronic storage device), similar to step 403.

Next, steps analogous to steps 407-415 may be repeated until convergence, with the exception that the steps are performed on the input cardiac CT image, rather than an image reconstruction (e.g., from step 403A). For example, a step similar to step 407 for image enhancement may include localizing the coronary artery vessel tree centerlines within the input cardiac CT image using any known technique. An enhancement step similar to step 409 may include matching zero or more coronary artery vessel tree centerline points from the collection of coronary artery models, to each coronary artery vessel tree centerline point found in the image input for enhancement. A metric may then be computed to describe similarity between each coronary artery vessel tree centerline point in the image and each point in the collection of models. Such a computation may be performed using any known graph matching technique. Example metrics include spectral correspondence, minimum edit distance, etc. In one embodiment, a threshold for the similarity metric may be determined. Then, a collection of matched points may be created based on the similarity metric, where the collection of matched points may contain zero or more matched points.

Merging, similar to step 411 (e.g., to determine a local image priors) may be done using the current input cardiac CT image and not the image reconstruction. For example, determining local image priors for each centerline point in an image enhancement process may include merging image regions associated with zero or more matched points. If zero matched points exist for a centerline point, that point may have no associated local prior, at least based on the input CT image and input set of coronary artery models. Methods for merging include: averaging the associated image regions, performing a weighted averaging of the associated image regions (in which weights are determined by the similarity metric of the associated points and/or predetermined image quality of the image (e.g., the input cardiac CT image) from which the associated image region was originally drawn), choosing an associated image region with greatest similarity to an image region local to the centerline point in the current image (e.g., input or merged image), a sparse linear combination of the associated image regions to match image region local to the centerline point in the current image, etc.

Performing image enhancement (as analogous to step 413) may include using image information and image priors, for example, blending the image priors in the current image (e.g., by applying an alpha compositing between the priors and the image). For optimization-based image enhancement methods, an extra term may be added into the optimization that penalizes the difference between the image and local priors. In one embodiment, convergence of the iterative process may be determined by measuring the difference between the enhanced image during two successive iterations (e.g., by computing a mean squared difference between intensity values at all voxels) and converging if the difference is below a predetermined threshold. Then, the method may include outputting a converged enhanced image (e.g., to an electronic storage device and/or display).

FIG. 4B is a block diagram of an exemplary method 420 for producing iterative reconstruction of abdominal images, according to one embodiment. For example, step 421 may include inputting abdominal CT image acquisition information, for example, on an electronic storage device. Step 423 may include inputting a set of organ models and associated image regions from the training phase (e.g., on an electronic storage device). Then, an initial abdominal CT image reconstruction may be performed, for instance, using acquisition information and any known iterative CT reconstruction technique (step 425).

Once such information has been acquired, steps 427-433 may be repeated until convergence. In one embodiment, step 427 may include localizing organs within the image reconstruction. This step may be performed using any known technique. Next, step 429 may include matching each organ surface mesh point found in the image to zero or more organ surface mesh points in the collection of organ mesh models. The matching may be performed using any graph matching technique to compute a metric describing similarity between the organ surface mesh point and each point in the collection. As previously described, example metrics include spectral correspondence, minimum edit distance, etc. Step 429 may further include determining a threshold of the similarity metric so that a collection of matched points is created, where the collection of matched points may contain zero or more matched points. Step 431 may include determining a local image prior for each surface mesh point, for instance, by merging the image regions associated with the zero or more matched points. If a surface mesh point corresponds to zero matched points, step 431 may include determining that the mesh point may have no associated local prior. Methods of merging may include those discussed previously, such as, for example, averaging associated image regions, determining a weighted averaging of associated image regions, where the weights are based on the similarity metric of associated points or the predetermined image quality of the image that provided the associated image region, choosing an associated image region with the greatest similarity to the image region local to the organ surface mesh in the current image reconstruction, and/or a sparse linear combination of the associated image regions to best match the image region local to the surface mesh point in the current image reconstruction. Step 433 may include performing an image reconstruction using the acquisition information and image priors (e.g., by blending the image priors with the current reconstruction, for instance, by applying an alpha compositing between the priors and the reconstructed image and/or for optimization-based iteration reconstruction methods, by adding an extra term into the optimization that penalizes the difference between the reconstructed image and the local priors). Step 435 may include determining convergence of the iterative process. For example, step 435 may include measuring the difference between the reconstructed image during two successive iterations (e.g., by computing a mean squared difference between intensity values at all voxels) and converging if the difference is below a predetermined threshold. Step 437 may include outputting the converged image reconstruction, for example, to an electronic storage device and/or display. In one embodiment, steps 427-433 may be repeated until convergence and steps 425-433 may be performed using a computational device.

The methods described in preparing sets of image regions associated with anatomical subdivisions to produce image reconstructions and/or enhancements may be applied to various forms of medical imaging. In one embodiment, the methods may comprise a training phase and a production phase. The training phase may include creating a set of associations between image regions and anatomical subdivisions, which form an "expected" set of information against which patient-specific information may be assessed. The production phase may include producing image reconstructions and/or enhancements based on the associations provided by the training phase.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of medical image reconstruction, the method comprising:
   acquiring a plurality of images associated with a target anatomy;
   determining, using a processor, one or more associations between subdivisions of localized anatomy of the target anatomy identified from the plurality of images, and local image regions identified from the plurality of images;
   performing an initial image reconstruction based on image acquisition information of the target anatomy; and
   updating the initial image reconstruction or generating a new image reconstruction based on the image acquisition information and the one or more determined associations.

2. The method of claim 1, wherein the determining step comprises:
    determining a localized anatomy of the target anatomy within each of the plurality of images; and
    subdividing the localized anatomy of each of the plurality of images into one or more of the determined subdivisions.

3. The method of claim 2, wherein the determining step further comprises:
    determining a local image region corresponding to each determined subdivision of localized anatomy of the target anatomy within each of the plurality of images.

4. The method of claim 2, further comprising:
    determining one or more image priors associated with one or more local image regions based on the one or more associations; and
    updating the initial image reconstruction or generating a new image reconstruction based on the one or more determined image priors.

5. The method of claim 1, further comprising:
    generating a model of local image regions associated with the respective localized anatomy, wherein the model is based on the local region of each of the images associated with the one or more subdivisions in the respective localized anatomy; and
    updating the initial image reconstruction or generating a new image reconstruction based on the generated model.

6. The method of claim 1, further comprising:
    localizing and subdividing anatomy within the initial image reconstruction;
    matching localized and subdivided anatomy with localized anatomy of the target anatomy identified from the plurality of images; and
    determining image priors for one or more regions based on the matching of localized and subdivided anatomy with localized anatomy of the target anatomy identified from the plurality of images.

7. The method of claim 6, further comprising:
    updating the initial image reconstruction or generating a new image reconstruction until a final image reconstruction converges based on the determined image priors.

8. The method of claim 1, wherein the localized anatomy is a coronary artery vessel tree, a portion of an organ, or a combination thereof.

9. A system for image reconstruction, the system comprising:
    a data storage device storing instructions for medical image reconstruction; and
    a processor configured to execute the instructions to perform a method including:
    acquiring a plurality of images associated with a target anatomy;
    determining, using a processor, one or more associations between subdivisions of localized anatomy of the target anatomy identified from the plurality of images, and local image regions identified from the plurality of images;
    performing an initial image reconstruction based on image acquisition information of the target anatomy; and
    updating the initial image reconstruction or generating a new image reconstruction based on the image acquisition information and the one or more determined associations.

10. The system of claim 9, wherein the at least one computer system is further configured for:
    determining a localized anatomy of the target anatomy within each of the plurality of images; and
    subdividing the localized anatomy of each of the plurality of images into one or more of the determined subdivisions.

11. The system of claim 10, wherein the at least one computer system is further configured for:
    determining a local image region corresponding to each determined subdivision of localized anatomy of the target anatomy within each of the plurality of images.

12. The system of claim 10, wherein the at least one computer system is further configured for:
    determining one or more image priors associated with one or more local image regions based on the one or more associations; and
    updating the initial image reconstruction or generating a new image reconstruction based on the one or more determined image priors.

13. The system of claim 9, wherein the at least one computer system is further configured for:
    generating a model of local image regions associated with the respective localized anatomy, wherein the model is based on the local region of each of the images associated with the one or more subdivisions in the respective localized anatomy; and
    updating the initial image reconstruction or generating a new image reconstruction based on the generated model.

14. The system of claim 9, wherein the at least one computer system is further configured for:
    localizing and subdividing anatomy within the initial image reconstruction;
    matching localized and subdivided anatomy with localized anatomy of the target anatomy identified from the plurality of images; and
    determining image priors for one or more regions based on the matching of localized and subdivided anatomy with localized anatomy of the target anatomy identified from the plurality of images.

15. The system of claim 14, wherein the at least one computer system is further configured to:
    updating the initial image reconstruction or generating a new image reconstruction until a final image reconstruction converges based on the determined image priors.

16. The system of claim 9, wherein the localized anatomy is a coronary artery vessel tree, a portion of an organ, or a combination thereof.

17. A non-transitory computer readable medium for use on a computer system containing computer-executable programming instructions for performing a method of medical image reconstruction, the method comprising:
    acquiring a plurality of images associated with a target anatomy;
    determining, using a processor, one or more associations between subdivisions of localized anatomy of the target anatomy identified from the plurality of images, and local image regions identified from the plurality of images;
    performing an initial image reconstruction based on image acquisition information of the target anatomy; and
    updating the initial image reconstruction or generating a new image reconstruction based on the image acquisition information and the one or more determined associations.

18. The non-transitory computer readable medium of claim 17, the method further comprising:
    determining a localized anatomy of the target anatomy within each of the plurality of images; and subdividing the localized anatomy of each of the plurality of images into one or more of the determined subdivisions.

19. The non-transitory computer readable medium of claim 18, the method further comprising:
   determining a local image region corresponding to each determined subdivision of localized anatomy of the target anatomy within each of the plurality of images.

20. The non-transitory computer readable medium of claim 18, the method further comprising:
   determining one or more image priors associated with one or more local image regions based on the one or more associations; and
   updating the initial image reconstruction or generating a new image reconstruction based on the one or more determined image priors.

* * * * *